(12) United States Patent
Vincent et al.

(10) Patent No.: US 7,966,068 B2
(45) Date of Patent: Jun. 21, 2011

(54) DETECTING A LEAD FRACTURE IN AN ACTIVE IMPLANTABLE MEDICAL DEVICE FOR CARDIAC PACING RESYNCHRONIZATION CARDIOVERSION AND/OR DEFIBRILLATION

(75) Inventors: Elodie Vincent, Antony (FR); Amel Amblard, Chatenay-Malabry (FR)

(73) Assignee: ELA Medical S.A.S., Montrouge (FR)

( * ) Notice: Subject to any disclaimer, the term of this patent is extended or adjusted under 35 U.S.C. 154(b) by 1068 days.

(21) Appl. No.: 11/750,519

(22) Filed: May 18, 2007

(65) Prior Publication Data

US 2007/0270914 A1 Nov. 22, 2007

(30) Foreign Application Priority Data

May 18, 2006 (FR) .................................... 06 04445

(51) Int. Cl.
*A61N 1/00* (2006.01)
(52) U.S. Cl. .......................................... 607/27; 607/28
(58) Field of Classification Search ................. 607/28
See application file for complete search history.

(56) References Cited

U.S. PATENT DOCUMENTS

| | | | |
|---|---|---|---|
| 5,304,208 A | 4/1994 | Inguaggiato et al. | |
| 5,496,351 A | 3/1996 | Plicchi et al. | |
| 5,755,742 A | 5/1998 | Schuelke et al. | |
| 5,776,168 A | 7/1998 | Gunderson | |
| 5,814,088 A | 9/1998 | Paul et al. | |
| 6,351,675 B1 * | 2/2002 | Tholen et al. | 607/59 |
| 6,892,092 B2 | 5/2005 | Surekha et al. | |
| 6,907,290 B2 | 6/2005 | Legay | |

FOREIGN PATENT DOCUMENTS

| | | |
|---|---|---|
| EP | 0515319 | 5/1992 |
| EP | 0655260 A2 | 5/1995 |
| EP | 1216723 | 12/2001 |
| EP | 1433496 A | 6/2004 |
| EP | 1438985 A | 7/2004 |
| EP | 1537894 A | 6/2005 |

* cited by examiner

*Primary Examiner* — Mark W Bockelman
*Assistant Examiner* — Elizabeth K So
(74) *Attorney, Agent, or Firm* — Orrick Herrington & Sutcliffe, LLP

(57) ABSTRACT

Detecting a lead fracture in an active implantable medical device for pacing, resynchronization and/or defibrillation of the heart. This device senses the heart rhythm through an endocardial lead comprising at least one endocardial electrode collecting the depolarization potentials, and detecting the myocardium contractions through an endocardial acceleration sensor. The device detects an incipient or total lead fracture by correlating the signals representative of successive ventricular and/or atrial depolarizations (P, R) with the signals representative of successive acceleration peaks (e.g., PEA I). In the case of a lack of correlation, a signal of suspicion of lead fracture is delivered, notably to generate an alarm signal through recording of markers in a memory of the device readable by an external programmer, RF transmission and/or production of an audible signal.

15 Claims, 2 Drawing Sheets

DETECTING A LEAD FRACTURE IN AN ACTIVE IMPLANTABLE MEDICAL DEVICE FOR CARDIAC PACING RESYNCHRONIZATION CARDIOVERSION AND/OR DEFIBRILLATION

FIELD OF THE INVENTION

The present invention relates to "active implantable medical devices" as such devices are defined by the Jun. 20, 1990 Directive 90/385/CEE of the Counsel of the European Community, and more particularly to implantable devices that continuously monitor a patient's heart rhythm, and deliver to the heart, if need be, electrical pulses for pacing, resynchronization, cardioversion and/or defibrillation, in case of detection by the device of a heart rhythm disorder.

BACKGROUND OF THE INVENTION

Analysis of the heart rhythm is made based upon electrogram (EGM) signals, collected by electrodes mounted on endocardial leads, implanted in the myocardium. From the EGM, one can measure the atrial and/or ventricular depolarization potential. These signals are then analyzed by the implantable device (IMD), which will, when appropriate, deliver to the patient an appropriate therapy. The therapy delivered may be in the form of, for example, low energy pulses (anti-bradycardia pacing or ventricular resynchronization pacing) or cardioversion or defibrillation shocks.

The implanted leads that are equipped with the electrodes usually have a very thin diameter and a high flexibility, so as to withstand the permanent mechanical constraints to which they are subjected, at the rhythm of heart beats. However, it may sometimes happen that, in spite of their mechanical characteristics, these leads present, over time, a degradation of their external insulation likely to affect sensing of the signal.

Thus, as an estimation, around 10% of the patients implanted with a defibrillator present fractures of the insulating material, or of the conductor, likely to affect sensing of the intrinsic heart rhythm.

These various types of degradations will hereinafter be referred to as a "fracture", including both fractures as such, (i.e., a total fracture) and incipient fractures or cracks appearing at the very early steps of such phenomena. Indeed, the lead fracture may appear in a very progressive manner, first by a cracking of the insulating material: the electrochemical potentials at the location of the rupture are then likely to disturb the signal of heart rhythm sensing, such disturbance being likely to be erroneously analyzed as a true depolarization of the ventricle.

This phenomenon is every bit as much pernicious as it often appears in a vary progressive manner, by disturbing only a few cycles in the beginning; moreover, if this phenomenon is synchronous with the contraction, it may be blanked over a relatively long duration, or even remain unobserved during patient follow-up examination performed by an electrophysiologist who directly analyzes, in real-time, the signals delivered by the IMD using an external programmer. Also, apart from having an intermittent character, a fracture may affect the ground conductor, in such a manner that it cannot be immediately detected when using a bipolar lead. It is then only once the fracture produces total rupture that the device will detect it, due to the absence of any input signal.

In the meantime, the risks of ventricular oversensing may mislead the device, with a consequent risk that it will lead to inappropriate therapies, for example, by wrongly inhibiting the anti-bradycardia pacing pulses or resynchronization therapies or, conversely, by wrongly delivering high energy shocks upon an erroneous diagnosis of a tachycardia or fibrillation, such shocks being particularly painful for the patient, and likely to be noxious.

OBJECTS AND SUMMARY OF THE INVENTION

It is, therefore an object of the present invention to provide improved detection of the risks of lead fracture at a time when such fractures are still manifesting themselves in an intermittent manner. More precisely, the present invention addresses the problem of discriminating the electrical disturbances generated by a lead fracture from among the cardiac depolarization signals effectively collected by the implanted lead, in order to prevent triggering of inappropriate treatments and/or to trigger an alarm long before the lead fracture definitely manifests itself in a total and permanent manner.

The starting point of the present invention lies in the observation that the depolarization, which is an electrical phenomenon sensitive to noise, is usually followed by a cardiac contraction, which is a mechanical phenomenon that is not affected by noise. Hence, by proceeding to a double sensing—of both depolarization and contraction—by separate devices, it is possible, in the presence of suspected disturbances such as those generated by a lead fracture, to obviate the doubt and confirm whether the sensed signal has been actually followed by a mechanical activity of the heart. Such a confirmation therefore properly represents a depolarization signal, and not a disturbance correlated to a lead fracture.

Sensing the heart's mechanical activity can notably be operated through the measurement of endocardial acceleration, by means of an accelerometer directly in contact with the heart muscle (usually placed at the level of the right ventricular apex). Indeed, it is known that endocardial acceleration reflects very precisely, and in real-time, the phenomena concurring to the mechanical operation of the heart. More precisely, the issued European patent EP 0,515,319, and its U.S. counterpart U.S. Pat. No. 5,304,208 (assigned to Sorin Biomedica S.p.A.) teach both a structure and a technique to collect an endocardial acceleration signal by use of an endocardial lead equipped with a distal pacing electrode implanted into the ventricle and integrating a micro-accelerometer allowing to measure the endocardial acceleration. The endocardial acceleration signal thus collected during a cardiac cycle notably presents two peaks corresponding to the two major noises that can be identified along each cycle of a normal heart:

the first endocardial acceleration peak ("PEA I") corresponds to the closure of mitral and tricuspid valves, at the beginning of the phase of iso-volumetric ventricular contraction (systole). The variations of this first peak are closely related to pressure variations in the ventricle (the amplitude of PEA I peak, being more precisely correlated to the positive maximum of pressure variation, dP/dt, in the left ventricle) and can therefore constitute a representative parameter for myocardium contractility.

The second peak of endocardial acceleration ("PEA II") corresponds to the closure of aortic and pulmonary valves, at the beginning of the diastole. It is produced by the brutal deceleration of moving blood mass in the aorta.

The issued European patent EP 0,655,260 and its U.S. counterpart U.S. Pat. No. 5,496,351 (assigned to Sorin Biomedica S.p.A.) describe a way to process the endocardial acceleration signal provided by the sensor located at the tip of the lead, so as to compute two respective values related to these peaks of endocardial acceleration. These documents propose to use the amplitude values of the peaks PEA I and PEA II in order to detect the heart disorders, and trigger or not a defibrillation therapy.

In the case of the present invention, the principle is to detect the presence or absence of a heart contraction, based upon the principle that each true heart cycle corresponds to one single cardiac contraction. The endocardial acceleration is analyzed, advantageously by detecting the presence or absence of a PEA I peak, to confirm the presence of a mechanical activity of the heart upon detection of a depolarization: such a detection that would not be followed by a mechanical activity of the heart may have been generated by a disturbance caused by a lead fracture, it is therefore suspect and shall be diagnosed as such.

The device of this invention is preferably of the same type as that described in EP 0,655,260 and U.S. Pat. No. 5,496,351 cited above. Broadly, the device comprises:

means for sensing a heart rhythm, comprising an implantable lead with at least one endocardial electrode able to collect the electrical potential related to the myocardium depolarizations, and one sensing circuit able to analyze the collected potentials and deliver a sequence of signals representative of the successive ventricular and atrial depolarizations, and means for sensing the myocardium contractions comprising an endocardial acceleration sensor, and means for determining at least one peak of endocardial acceleration over one given cardiac cycle and delivering a sequence of signals representative of successive acceleration peaks.

In a manner characteristic of the invention, it is also proposed to include a means for detecting a fracture of said lead, comprising means for receiving as input, and correlating together, said signals representative of the depolarizations and said signals representative of the peaks of endocardial acceleration and, in the case of a lack of correlation, delivering a signal of suspicion of a lead fracture.

In one embodiment, the device can advantageously comprise two distinct endocardial leads, one equipped with said endocardial electrode, the other with said endocardial acceleration sensor. In this embodiment, the means for detecting a lead fracture detects a fracture in said first lead.

The device may further comprise means for measuring the lead impedance, triggerable in response to the delivery of an indicator of lead fracture.

Preferably, the device comprises means for producing an alarm signal in response to the recurrent delivery of a selected number of indicators of lead fracture suspicion during a predetermined period of time. The indicators may be manifested through recording of specific markers in a memory of the device, readable by an external programmer, RF transmission and/or production of an audible signal.

The delivery of a signal of suspicion of lead fracture is notably conditioned by the detection:

of a sequence of acceleration peaks with a stable amplitude and/or stable coupling intervals, of a sequence of acceleration peaks with a frequency that is lower than a limiting value representative of a threshold of detection of tachycardiae, of a sequence of depolarizations presenting successive coupling intervals that are short and variable, and/or of a sequence of depolarizations presenting a signal amplitude that is lower than a predetermined sensing threshold.

The acceleration sensor can be a sensor able to assess the acceleration at the level of a ventricle, an atrium, or a peripheral heart blood vessel.

BRIEF DESCRIPTION OF THE DRAWINGS

Further features, advantages and characteristics of the present invention will become apparent to a person of ordinary skill in the art in view of the following description of a preferred embodiment of a device of the invention, made with reference to the attached figures, in which like reference characters refer to like elements, and in which.

DETAILED DESCRIPTION OF THE INVENTION

Regarding the software-related aspects thereof, the invention can be implemented by means of an appropriate programming of the software of a known active implantable device, for example, of the pacemaker, or defibrillator/cardiovertor type, comprising means for acquiring a signal provided by endocardial leads and/or one or more implanted sensors.

The invention can notably be applied to the implantable devices such as the Ela Symphony and Rhapsody brand pacemakers, marketed by ELA Medical, Montrouge, France. These devices are equipped with programmable microprocessors, including circuits intended to acquire, format and process electrical signals collected by implanted electrodes, and deliver pacing pulses to these electrodes. It is also possible to upload towards these devices, by telemetry, software routines (updates, enhancements and new programs) that will be stored in internal memory and run so as to implement among other things the features of the invention, described in more detail below. Implementing the features of the invention into these devices is deemed to be well within the abilities of a person of ordinary skill in the art, and will therefore not be described in detail in this document.

Figure 1:
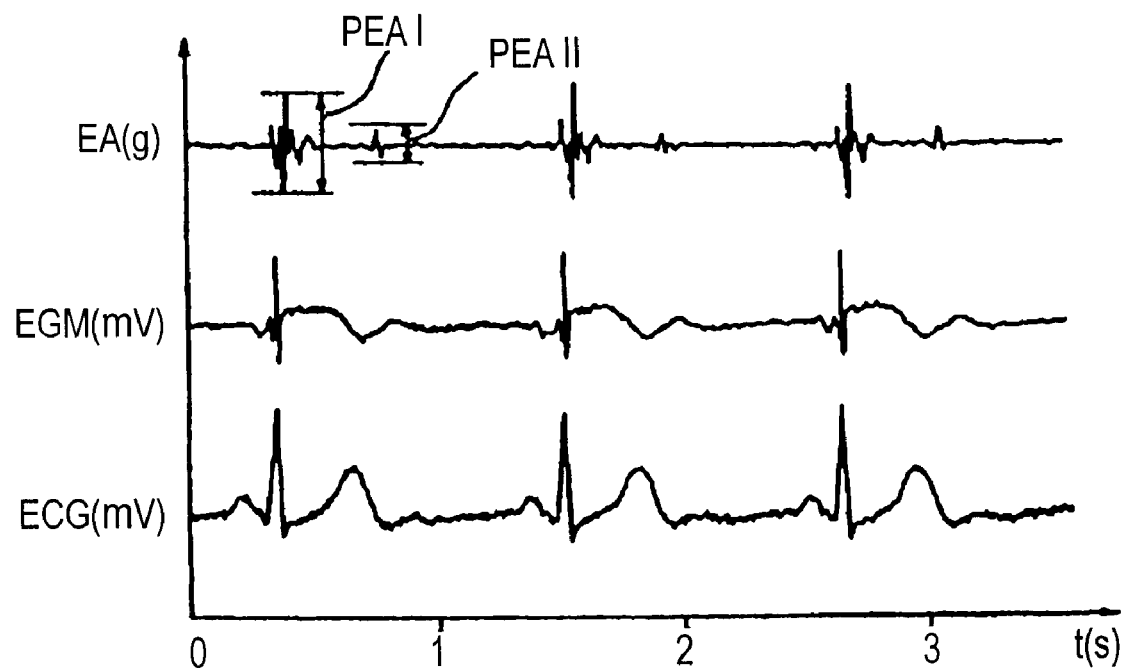
FIG. 1 is a time diagram showing, over three successive cardiac cycles, the variations of an endocardial acceleration as well as the electrogram and surface electrocardiogram in a representative signal.
Figure 2:
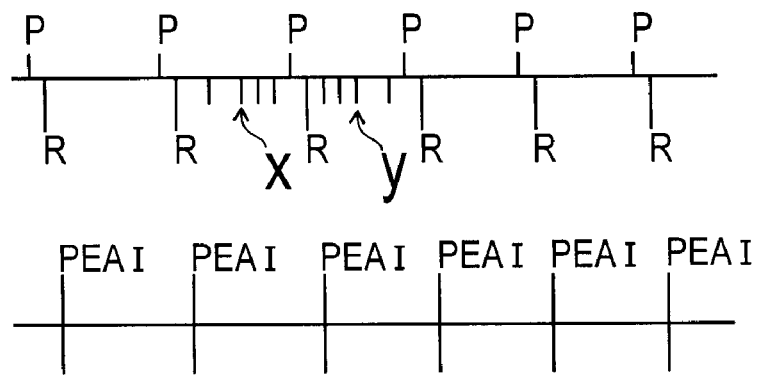
FIG. 2 is a time diagram, showing, over six successive cardiac cycles: the different collected signals representative of successive depolarizations and the signal indicating the presence of an endocardial acceleration peak.
Figure 3:
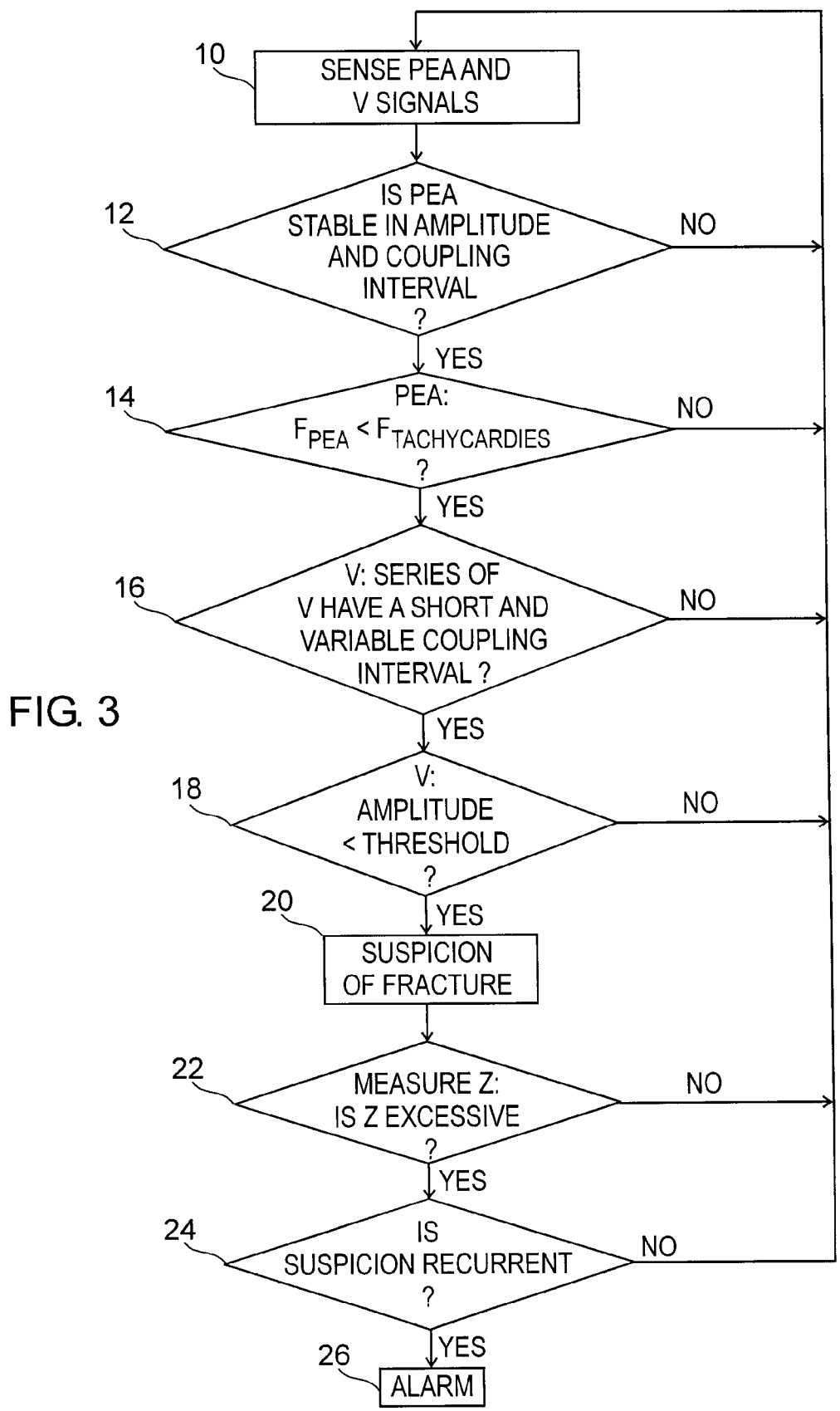
FIG. 3 is a flowchart showing the successive steps of an analysis of an implementation of the invention.

One will now describe an example of a preferred embodiment of the device of the present invention with reference to FIGS. 1-3. With reference to FIG. 1, the upper curve shows the variations of endocardial acceleration (EA), measured through a sensor of the type described in EP 0,515,319 and U.S. Pat. No. 5,304,208 cited above, embedded in the tip of an endocardial lead placed in the apex of the ventricle.

FIG. 1 also shows the electrogram (EGM) traces, i.e., of the electrical signal collected through the distal electrode of the same lead, and corresponding surface electrocardiogram (ECG), over three successive cardiac cycles. As explained above, the trace of acceleration presents two successive complexes or peaks of endocardial acceleration (PEA), parameters of which (amplitude, width and time position, that is: moment of occurrence) can be determined by means of an appropriate processing of the signal provided by the acceleration sensor, as described in EP 0,655,260 and U.S. Pat. No. 5,496,351 cited above.

The device uses the parameters correlated to the endocardial acceleration thus collected, notably the occurrence of PEA I peak (indicated by the time position of this peak), in order to confirm or not the presence of a mechanical activity of the heart.

The first line of FIG. 2 shows the succession of atrial (P) and ventricular (R) events, over six successive cardiac cycles, for a patient presenting a normal sinus rhythm.

Collection of these signals may be disturbed by electrochemical potentials appearing at the location of a fracture (as defined to be a total or incipient fracture) of the lead, potentials that can be seen as disturbances, such as those illustrated in X and Y, likely to be (wrongly) interpreted by the IMD as ventricular events leading to an erroneous suspicion of a brutal increase of the ventricular rate, similar to what could happen in case of ventricular fibrillation.

However, the sequence of acceleration peaks (the second line in FIG. 2) is not affected by lead fracture, for it reflects the sensing of a purely mechanical activity, as explained above.

The steady character of the contractions allows to obviate the suspicion of ventricular fibrillation and to suspect the presence of a fracture along the lead.

One will now describe, with reference to the flowchart on FIG. 3, a preferred embodiment of the correlation between the signals representative of the depolarizations (Vs) (the first line in FIG. 2) and those representative of the acceleration peaks (PEAs) (the second line in FIG. 2). To that end, in this embodiment, the endocardial lead equipped with the endocardial acceleration sensor is different from the lead collecting the EGM signals.

The first step (10) consists of collecting in a continuous way, the endocardial acceleration signals and the ventricular depolarizations, the analysis being performed for each cardiac cycle.

The device determines, based upon those measurements, a first series of signals representative of the ventricular depolarizations (V), and a second series of signals representative of the acceleration peaks (PEA) (advantageously the PEA I peak).

The device can notably use the endocardial acceleration signals at the level of the right ventricle. But the invention can also be implemented by using the signals representative of the endocardial acceleration that is level with:
  an atrium,
  the left ventricle,
  a blood vessel that is peripheral to the heart, i.e., a vessel located on the heart or at immediate proximity thereof (in contact with the heart wall).

The first phase of the analysis (step 12) is to determine whether the PEA signals are stable in amplitude and/or in coupling intervals (the coupling interval being the time period between two peaks relating to successive cycles). The condition of stability in amplitude means, for example, that the PEA I peak amplitude does not vary by more than x % compared to the average of the previous y cycles. The condition of stability of coupling intervals means, for example, that the coupling interval does not vary by more or less z milliseconds, for instance plus or minus 30 milliseconds from one cycle to the next.

In the presence of a stable PEA rhythm, revealing regular contractions, the device determines (step 14) whether the rate of these contractions (frequency of PEA peaks or $f_{pea}$) is lower than a limiting rate, lower than the detection zone of tachycardiae ($f_{tachycardiae}$).

If not, then the heart rhythm is probably a confirmed tachycardia, for which a therapy shall be considered, with no need to perform the fracture analysis any further.

Otherwise, in the presence of a rhythm of contractions that is sufficiently low, the device examines (step 16) whether it is in presence of a series of ventricular events with a short and variable coupling interval (the criterion of "short coupling" means that the coupling intervals between successive ventricular events are lower than a given threshold, and the criterion of "variable coupling" means that the differences between the coupling intervals are higher than a given threshold over a predetermined number of successive cycles).

If the analysis of the ventricular depolarizations reveals (at step 16) a fast and unstable rhythm, then the device determines whether the amplitudes of these depolarizations are below a given threshold (step 18). If so, it is probable that these signals do not represent true depolarizations, and the fracture diagnosis is not performed any further. It is also possible, at this step, to perform the test on a plurality of ventricular events, the test consisting of determining the number of ventricular events presenting an amplitude lower than the predetermined threshold, and to withdraw performing the diagnosis any further only if the number of such events is higher than a given number, so as to prevent the diagnosis from being interrupted by a reduced number of atypical events.

If the conditions stated at steps 12 to 18 are fulfilled, then the device determines that there is a suspicion of fracture (step 20), for example, by setting a specific indicator.

This fracture suspicion can in particular be used for triggering a lead impedance measurement (step 22) through a known process, for instance of the same type as described in European patent EP 1,216,723 and its U.S. counterpart U.S. Pat. No. 6,907,290 (commonly assigned herewith to ELA Medical). These patents describe a circuit and technique for evaluating the complex impedance of a lead through applying specific pacing pulses and analyzing the resulting variations of the sensed signal.

If this impedance measurement indeed reveals a defect (step 22), and the fracture suspicion diagnostic is a recurrent diagnostic (step 24), then the device considers that there is a confirmed fracture and generates an alarm signal (step 26). For example, a lead impedance measurement is typically made every 6 hours. If on the occurrence of X out of Y measurements, the impedance measurement reveals a fracture, whether the measurement is triggered by a suspicion of fracture or a periodic lead impedance measurement, the fracture suspicion is deemed recurrent. By way of illustration, if out of four consecutive measurements (Y=4), there are 3 or 4 (X=3 or X=4) consecutive fractures detected, then the suspicion of fracture is determined to be recurrent.

Step 24, of checking whether the suspicion is recurrent or not, allows to obviate the case of certain disturbance signals appearing in a punctual manner and producing sensing artifacts that are not correlated to a lead fracture. Indeed, a fracture usually appears in a progressive manner and, at least in the beginning, in an intermittent manner. It is the recurrence of the disturbances induced by the rupture currents that will allow one to confirm that there is indeed an actual lead rupture, rather than extrinsic noise artifacts, such as electromagnetic interference coming from electronic surveillance equipment, daily-life electrical apparatuses, electro-surgical instruments, communication systems, etc.

The alarm signal generated at step 26 can notably comprise:
  the recording of a marker in a memory of the device, allowing to warn the electrophysiologist during a further routine follow-up visit, that a fracture phenomenon has been diagnosed by the device, and/or
  the production by a "buzzer", of a signal audible to the patient, in order to warn him with no delay, and/or
  the emission of a signal through RF transmission means.

One skilled in the art will appreciate that the present invention can be practiced by other than the embodiments described herein, which embodiments are presented for purposes of illustration and not of limitation.

We claim:

1. An active implantable medical device for pacing, resynchronization, cardioversion and/or defibrillation of a heart, comprising:

means for sensing a heart rhythm, comprising an implantable lead having at least one endocardial electrode collecting electrical potentials representative of myocardium depolarizations, and a sensing circuit analyzing the collected electrical potentials and delivering a sequence of signals that are representative of successive cardiac depolarizations;

means for detecting myocardium contractions, comprising an endocardial acceleration sensor adapted to be in direct contact with a tissue of the heart, and means for determining at least one peak of endocardial acceleration over one given cardiac cycle and delivering a sequence of signals that are representative of successive endocardial acceleration peaks (PEA); and means for detecting a fracture of said lead, comprising:
means for receiving as an input, and correlating together, said sequence of signals representative of the successive cardiac depolarization, and said sequence of signals representative of the successive endocardial acceleration peaks; and
means responsive to a lack of correlation, for delivering an indicator of suspicion of a fracture of said lead.

2. The device of claim 1, further comprising two distinct endocardial leads, a first lead being equipped with said endocardial electrode and a second lead being equipped with said endocardial acceleration sensor, said means for detecting a fracture further comprising means for detecting a fracture of said first lead.

3. The device of claim 1, further comprising means for measuring lead impedance in response to the delivered indicator of a lead fracture suspicion.

4. The device of claim 1, further comprising means for generating an alarm signal in response to a recurrent delivery of indicators of lead fracture suspicion over a predetermined duration.

5. The device of claim 4, wherein said means for generating an alarm signal comprises means for recording a marker representative of said alarm signal in a memory of the device, said memory being readable by an external programmer.

6. The device of claim 4, wherein said means for generating an alarm signal further comprises means for providing an RF transmission representative of said alarm signal.

7. The device of claim 4, wherein said means for generating an alarm signal further comprises means for generating an audible signal representative of said alarm.

8. The device of claim 1, wherein said means for delivering an indicator of lead fracture suspicion further comprises means for conditioning the delivery of an indicator of lead fracture to the detection of a sequence of acceleration peaks that is stable in terms of amplitude and/or coupling intervals.

9. The device of claim 1, wherein said means for delivering an indicator of lead fracture suspicion further comprises means for conditioning the delivery of an indicator of lead fracture to the detection of a sequence of acceleration peaks with a frequency that is lower than a limiting frequency representative of a threshold for the detection of tachycardia.

10. The device of claim 1, wherein said means for delivering an indicator of lead fracture suspicion further comprises means for conditioning the delivery of an indicator of lead fracture to the detection of a sequence of depolarizations presenting successive short and variable coupling intervals.

11. The device of claim 1, wherein said means for delivering an indicator of lead fracture suspicion further comprises means for conditioning the delivery of an indicator of lead fracture to the detection of a sequence of depolarizations presenting a signal amplitude lower than a predetermined sensing threshold.

12. The device of claim 1, wherein the acceleration sensor further comprises a sensor for measuring acceleration level with a heart ventricle.

13. The device of claim 1, wherein the acceleration sensor further comprises a sensor for measuring acceleration level with a heart atrium.

14. The device of claim 1, wherein the acceleration sensor further comprises a sensor for measuring acceleration level with a blood vessel that is peripheral to the heart.

15. The device of claim 1, wherein the means for delivering a sequence of cardiac depolarizations further comprises means for detecting successive ventricular depolarizations.

* * * * *